(12) United States Patent
Bobka et al.

(10) Patent No.: US 7,785,574 B2
(45) Date of Patent: Aug. 31, 2010

(54) WATER-FREE PREPARATION

(75) Inventors: Ernst Bobka, Erlangen (DE); Thomas Gibtner, Eckental (DE); Michaela Mara, Nuremberg (DE)

(73) Assignee: Schwan-STABILO Cosmetics GmbH & Co. KG, Heroldsberg (DE)

( * ) Notice: Subject to any disclaimer, the term of this patent is extended or adjusted under 35 U.S.C. 154(b) by 930 days.

(21) Appl. No.: 10/881,411

(22) Filed: Jun. 30, 2004

(65) Prior Publication Data

US 2005/0226832 A1    Oct. 13, 2005

(30) Foreign Application Priority Data

Apr. 7, 2004  (DE) ............. 10 2004 017 177

(51) Int. Cl.
*A61Q 3/00*   (2006.01)
*A61Q 1/02*   (2006.01)
*A61Q 19/04*  (2006.01)
*A61K 8/02*   (2006.01)

(52) U.S. Cl. .................. 424/61; 424/63; 424/64; 424/401

(58) Field of Classification Search ............ 424/401, 424/61, 63, 64
See application file for complete search history.

(56) References Cited

U.S. PATENT DOCUMENTS

| | | | |
|---|---|---|---|
| 5,690,918 A | | 11/1997 | Jacks et al. |
| 5,725,845 A | * | 3/1998 | Krog et al. ............. 424/64 |
| 5,932,197 A | * | 8/1999 | Arnaud ............... 424/64 |
| 6,162,421 A | * | 12/2000 | Ordino et al. ........... 424/64 |
| 6,203,780 B1 | | 3/2001 | Arnaud et al. |
| 6,395,263 B1 | | 5/2002 | Nichols et al. |
| 6,682,748 B1 | | 1/2004 | De La Poterie et al. |
| 6,695,510 B1 | | 2/2004 | Look et al. |
| 2002/0058054 A1 | | 5/2002 | Arnaud |
| 2002/0159960 A1 | * | 10/2002 | Scancarella et al. ........ 424/64 |
| 2002/0176831 A1 | * | 11/2002 | Wang et al. ............ 424/63 |
| 2003/0054019 A1 | * | 3/2003 | Aronson et al. .......... 424/401 |
| 2003/0068344 A1 | | 4/2003 | Ferrari et al. |

FOREIGN PATENT DOCUMENTS

| | | |
|---|---|---|
| DE | 697 05 379 | 10/2001 |
| DE | 696 26 956 | 1/2004 |
| EP | 1 325 730 | 7/2003 |
| EP | 1 358 866 | 11/2003 |
| WO | WO 03/000223 | 1/2003 |

* cited by examiner

*Primary Examiner*—Johann R Richter
*Assistant Examiner*—Luke E Karpinski
(74) *Attorney, Agent, or Firm*—Bachman & LaPointe, P.C.

(57) ABSTRACT

Described is a water-free preparation, in particular for application to the lips, which contains a silicone-free phase which contains at least one polybutene and/or polyisobutene, at least one isoparaffin, at least one wax and/or wax ester and optionally conventional adjuvant and additive substances and a silicone-bearing phase which contains at least one fluorosilicone, at least one dimethicone, at least one dimethiconol and optionally a particulate phase and fillers.

32 Claims, No Drawings

WATER-FREE PREPARATION

The present invention concerns a water-free preparation, in particular for application to the lips, which is made up of two components, wherein said components are distinguished in that they form a stable homogeneous composition which upon application to the skin, in particular the lips, separates into two layers so that disposed on the skin or lips in mutually superposed relationship are firstly a glossy layer and thereover a second layer for preventing removal of the glossy layer.

The preparation according to the invention combines the properties of a 'coloring' lipstick with those of a lip gloss. Lipsticks for coloring the lips have already long been known and endeavours have also already long been made to provide lipsticks which, after being applied to the lips, remain at the applied location and are no longer transferred on to contact surfaces which come into contact therewith. Lip gloss has also long been known. In general, lip gloss is applied over a layer of lipstick in order to enhance the gloss and to protect the lipstick which is therebeneath. The known lip gloss products which impart a high level of gloss to the lips are generally very sticky, they do not remain adhering to the lips very long as they are easily removed and in addition they have to be applied in a second layer. Combinations of lipstick and lip gloss have already been proposed in the state of the art. Thus for example U.S. Pat. No. 6,395,263 discloses a method of coloring the lips, in which firstly a fluid coloring agent which besides cosmetic pigments contains an alcohol-soluble resin and an organic solvent is applied and then a lip gloss is put on, wherein the liquid coloring preparation contains between 50 and 99% of organic solvent, in particular ethanol. As alcohol, in particular ethanol, has a strongly dehydrating effect, that agent is felt to be unpleasant on the lips, in particular if the lips are dry and chapped. In addition that high proportion of alcohol is also undesirable for people with alcohol problems.

In addition US No 2003/0 068 344 discloses a method of making up skin and lips, which involves applying for example to the skin or the lips to form a first layer firstly a composition which contains dispersed polymer particles in a liquid phase and then after drying of that first composition a second composition for producing a second layer which has a silicone-based phase. The disadvantage of that composition is that the second layer serving as lip glass can be applied only when the first layer is dried, which is complicated and time-consuming.

Now the object of the invention is to provide a composition for application to the skin, in particular the lips, which adheres to the place of application for a long time, which is not transferred on to other contact surfaces and which retains the gloss without substantial changes over a long period of time. Another object is to provide a preparation which is easy to use as a one-phase product, which can be easily and uniformly applied to the lips, which does not produce any feelings of tension or dries out the lips, and which in addition affords the possibility of producing special effects on the lips.

Those objects are attained by a product. In accordance with the invention wherein there is provided a water-free preparation, in particular for application to the lips, including a) a silicone-free phase which contains at least one polybutene and/or polyisobutene, at least one isoparaffin, at least one wax and/or wax ester and optionally conventional adjuvant and additive substances, and b) a silicone-bearing phase which contains at least one fluorosilicone, at least one dimethicone, at least one dimethiconol and optionally a particulate phase and fillers.

It was surprisingly found that the product in accordance with the invention affords is highly stable and which can be stored as a homogeneous composition over a prolonged period of time without separating but which, as soon as it is applied to the lips, separates into two different phases and forms a lower, optionally colored and/or glossy layer which adheres strongly to the lips and which possibly contains coloring agent, and an upper layer which is disposed as a protective layer over the lower phase and possibly imparts special effects. The first layer has a very high level of affinity to the skin and therefore enjoys very good adhesion thereto. In comparison the second layer is a kind of barrier layer which prevents the first layer from being removed and thereby protects it. The second layer can also perform yet a further function which is particularly important for achieving special effects. By virtue of their composition the first and second layers are relatively incompatible and are deposited in mutually superposed relationship without mixing. As a result the contents contained in the respective layers are also kept separate. That can be utilised for example for using matt and glossy pigments in separate layers so that the matt pigments can give color without adversely affecting the gloss of the glossy pigments.

An advantage of the preparation according to the invention is that it is free of triglyceride-bearing oils which are a cause of the migration of lipstick materials.

It is therefore essential for the invention that the two components are sufficiently incompatible and that upon application to the lips the first component separates from the second, forming two layers. On the other hand the two components must be so compatible with each other that the composition remains homogeneous and of one-phase nature in the container in which it is stored. The contents which are selected for the two components ensure that those properties are attained.

The water-free preparation according to the invention can be applied to skin and mucous membranes and is particularly suitable for application to the lips. The preparation according to the invention comprises at least two components, a silicone-free phase and a silicone-bearing phase which are necessary to achieve the desired effects. In that respect component a) forms the lower layer which adheres to the skin or mucous membrane while component b) forms the protective layer thereover. In a preferred embodiment the lower layer which is formed from component a) is colored and imparts the color impression which the preparation is intended to have. The upper phase which is formed from component b) is either transparent or imparts special effects so that the color of the lower layer can appear therethrough and is possibly boosted or caused to shine with a gloss by virtue of effect-forming agents in the component b).

The preparation is water-free, the two components are each flowable to pasty and can contain solvents for solubilisation purposes. An embodiment uses solvents whose volatility is such that they scarcely evaporate at ambient temperature, but are evaporated at body temperature for example within about 24 hours.

The component a) of the preparation according to the invention contains constituents which adhere well to the skin and in addition can absorb and hold coloring agents. A constituent contained in component a) is at least one polybutene and/or polyisobutene which provides for the adhesion effect. Polybutenes and polyisobutenes are well-known in the field of cosmetics and are commercially available. Polybutenes and polyisobutenes with a weight-average molecular mass of less than 1,000,000, preferably between 1,000 and 500,000, are suitable. It has been found that particularly good results are achieved when using a combination of at least two polybutenes or polyisobutenes, of which one has a lower molecular mass and the other a higher molecular mass. For example a polybutene or polyisobutene is suitable, with a weight-average molecular mass of less than one million, preferably in the range of between 10,000 to 500,000, particularly preferably between 15,000 and 100,000 as the polymer of higher molecular mass which can optionally be combined with a further polybutene and/or polyisobutene of a molecular mass of less than 30,000, preferably between 1,000 and 25,000, particularly preferably between 2,000 and 10,000.

If in an embodiment component a) involves using a combination of two polymers selected from polybutene and polyisobutene of different molecular masses, the quantitative ratio of polymer of higher molecular mass to polymer of lower molecular mass is suitably in a range of between 15:1 and 1:10, preferably between 10:1 and 3:1.

As a structure-generating agent component a) of the preparation according to the invention further contains a wax and/or a wax ester. The waxes and wax-like constituents usually employed in cosmetic compositions are suitable here. It is possible to use vegetable, animal, mineral and/or synthetic waxes and/or long-chain wax esters. Examples of waxes are carnauba wax, candellila wax, rice wax, Japan wax, ouricurri wax, beeswax, shellac wax, ozocerite, montan wax, microcrystalline wax, polyethylene wax but also wool wax. Suitable wax esters are in particular esters which were formed from a saturated or a singly or more unsaturated straight-chain or branched fatty acid with a chain length of between C12 and C40 and a saturated or singly or multiply unsaturated straight-chain or branched fatty alcohol of a chain length of between C12 and C40. Examples of wax esters that can be mentioned are behenyl behenate, behenyl erucate, stearyl stearate, isostearyl stearate, isostearyl isostearate, behenyl stearate, stearyl behenate, jojoba oil and hydrated jojoba oil. It is also possible to use mixtures of the specified waxes and wax esters.

In accordance with the invention at least one long-chain hydrocarbon is used for solubilisation of the component a) and as a constituent which provides for a suitable viscosity. Appropriately at least one isoparaffin is used, which preferably involves such a volatility that it remains contained in a stable fashion in the composition while it evaporates upon application to the lips, that is to say at body temperature. Preferred is an isoparaffin or a combination of isoparaffins with a vapor pressure in the range of between 0.1 and 20 kPa at 25° C., preferably between 0.2 and 10 kPa and particularly preferably between 0.5 and 5 kPa. Isoparaffins of a chain length of between C8 and C30, preferably between C10 and C24, have proven to be suitable, in which respect mixtures can optionally be employed. A particularly suitable isoparaffin is one with a chain length in the range of between C18 and C24 which also makes the texture soft and ductile.

The constituents of the component a), in particular polybutene and/or polyisobutene, provide for adhesion to the skin and at the same time for the gloss of the applied layer. That gloss is so great that it is maintained even when there is a second layer disposed thereover.

Component a) may also contain further constituents which are conventional in cosmetic compositions such as fillers, thickening agents, flavoring substances and fragrances, antioxidants and preserving agents.

Preserving agents are not necessary per se for the water-free composition according to the invention as the risk of microbial contamination is slight. If however preservation is desired, that can be implemented in the usual manner. The antioxidants used can be those which are conventionally employed in cosmetic compositions, preferably in the amounts which are usually employed. Antioxidants are preferably added when there are unsaturated compounds in the wax phase.

In an embodiment the composition according to the invention can be used with a component a) which contains the above-discussed constituents and then imparts to the lips only gloss and optionally the effects to be achieved with component b). It is also optionally possible to add sun-protection agents and care constituents in order to provide a pencil which cares for and protects the lips and which causes the lips to appear glossy.

Preferably however the preparation according to the invention is used in the form of a 'coloring' lipstick and for that purpose component a) is provided with coloring agents. The coloring agents involved may be the dyestuffs or pigments which are usually employed for lipsticks. It is possible to make full use of the whole range of colors in this case, depending on the respective fashion and taste. In that respect yellow, red, orange-colored, violet and blue shades are to the fore. The pigments and dyestuffs which are suitable here are known per se to the man skilled in the art. It is possible to mention here as examples the C.I. pigments Red 57:1, Red 49:1, Red 48:1, Red 52:1, Red 41, Red 3, Red 23, Red 112, Red 169, Orange 16, Orange 5, Violet 1, Violet 23, Green 7, Blue 61, Blue 62, Blue 15:1, White 6, Yellow 3, Yellow 13, Yellow 55, Yellow 126, FD & C Red 3, D & C Red 6, 7, 30, 36, 40, FD & C Yellow 5, 6; D & C Red 21 (CI 45 380), D & C Orange 5 (CI 45 370), D & C Red 27 (CI 45 410), D & C Orange 10 (CI 45 425), D & C Red 3 (CI 45 430), D & C Red 7 (CI 15 850:1), D & C Red 4 (CI 15 510), D & C Red 33 (CI 17 200), D & C Yellow 5 (CI 19 140), D & C Yellow 6 (CI 15 985), D & C Green 5 (CI 61 570), D & C Yellow 10 (CI 77 002), D & C Green 3 (CI 42 053), D & C Blue 1 (CI 42 090), fluorescing dyestuffs such as C.I. 45380, 45370:1, 47000, 47005, 42090, 60730 or 61570. Inorganic pigments such as titanium dioxide, zinc oxide, cerium oxide, black, red, yellow and brown iron oxides, chromium oxide, chromium hydroxide, manganese violet, ultramarine and further coloring pigments can also be mentioned. Lakes of organic coloring agents with aluminum, barium, calcium, zirconium or strontium are also possible. The list is only by way of example and is in no way definitive. Organic coloring agents can also be used when attached to carriers. The suitable coloring agents are usually selected according to the respective desired color shade, depth of color and also on the basis of the extent to which they are permitted by national or regional legislation in the field of cosmetics. In addition suitable coloring agents can be incorporated to achieve special coloring effects, for example coloring shading effects which are visible in black light, that is to say in UV light. Coloring agents of that kind are commercially available, for example immobilised in plastic matrices. Fluoresceins, quinoline dyestuffs, triphenylmethane dyestuffs and anthraquinone dyestuffs can be named as dyestuffs which produce luminescent, in particular fluorescent or phosphorescent effects or effects which light up under UV light. They can be attached to a polymer matrix which is also known as 'Polyester-3' to the man skilled and active in the relevant art. Plastic matrices of that kind can be produced for example by the reaction of ethylene glycol, cyclohexane dimethanol, terephthalic acid, isophthalic acid and norbornane diamine in the presence of the dyestuff. At any event the coloring agents belonging to the class of flat pigments should be incorporated into component a).

The preparation according to the invention and in particular the component a) may contain further particulate colored or neutral constituents such as for example nanopigments or light-protection agents in the form of titanium dioxide and/or zinc oxide. In that respect the particles are of a size in the nanometer range, for example suitable particles are of a size in the range of between 5 and 25 nm.

Pigments and coloring agents are contained in the preparation according to the invention in the amounts usually employed in cosmetics. In that respect the proportion of the pigments is respectively selected in a wide range in accordance with color shade and depth of color. A range of between 1 and 50% by weight with respect to the overall composition is considered in that respect. Preferably the pigments are used in a proportion of between 5 and 40% by weight, particularly preferably between 10 and 30% by weight.

As the preparation according to the invention is to be applied to and adhere to the lips, it should be of a thickly liquid to pasty viscosity. Preferably therefore the preparation according to the invention is in the form of a homogeneous thickly liquid to pasty paste, the viscosity of which, measured with a Bohlin rheometer, with a cone-plate system, 4°/40 mm, is in a range between 500 mPa s and 1500 Pa s. At a shearing rate of 0.001 per second the rest viscosity should preferably be in a range of between 10 and 1500 Pa s, particularly preferably between 50 and 1200 Pa s and in particular between 100 and 600 Pa s. At a shearing rate of 1/s the viscosity is in a range of between 500 mPa s and 200 Pa s, preferably between 2 and 150 Pa s, particularly preferably between 10 and 90 Pa s.

To adjust the viscosity the component a) may also contain thickening agents or fillers, as usual additives. The thickening agents used can be such agents which are known in the state of the art and which in water-free systems act as thickeners, in which respect they are used in such amounts that the desired viscosity is attained. Suitable examples for that purpose are talcum, kaolin, starch and modified starch, polytetrafluoroethylene powder, nylon powder, boron nitride, insoluble metal soaps such as Mg stearate, Ca stearate, Sr stearate, Zn stearate and so forth.

Flavoring substances and fragrances serve to improve the taste and scent of the pencil. Flavoring substances which can be used are usual ethereal oils such as peppermint, spearmint, cherry, strawberry flavorings etc. For example phenyl ethanol can be mentioned as a fragrance. The fragrances and flavoring substances are used in the amounts which are suitable for achieving the effect, which are usually below 1% by weight with respect to the overall composition.

The preparation according to the invention may optionally also contain emulsifiers and/or tensides, in particular anionic, non-ionic, cationic and/or amphoteric tensides. It will be noted however that the tensides used should not detrimentally influence the separability of the component a) and the component b), that is to say they should not contribute to such compatibilisation that the two components no longer separate when they are applied to the lips.

Further constituents which can be incorporated into the component a) of the preparation according to the invention are sun-protection agents and UV absorbers as are known in this field.

The second component which is used according to the invention, as already stated above, serves to seal the firmly adhering component a). It should form a layer which is disposed over the layer formed by the component a) and which no longer separates from the subjacent layer and which also can no longer be displaced thereon. In addition it should be transparent so that gloss and color which are contributed by the lower layer still remain visible. In addition however the layer contributed by component b) can contribute further effects as is discussed hereinafter.

The component b) is a silicone-bearing phase made up from a fluorine-bearing silicone and a linear silicone. Those silicones are generally capable of flow or capable of being spread. If silicones which are not spreadable are to be used, they can be solubilised with a suitable solubilisation agent such as a volatile silicone, for example cyclomethicone.

In order to achieve the effect which is essential according to the invention, namely separation of the preparation to form two layers upon application to the lips, the second component of the preparation must be a silicone-bearing phase. The main proportion of the component b) is at least one dimethicone and at least one dimethiconol. Linear polydimethylsiloxanes are referred to as dimethicone while dimethiconol stands for polydimethylsiloxanes with terminal hydroxyl groups. Both dimethicone and also dimethiconol are so selected that they are not volatile either at storage temperature or at body temperature, that is to say at room temperature they should have a vapor pressure below 20 kPa at 20° C., preferably below 2 kPa and particularly preferably below 1 kPa. Polydimethylsiloxanes are well-known to the man skilled in the art and the qualities which are suitable for cosmetic compositions are also considered for the present invention. Straight-chain polydimethylsiloxanes with terminal methyl groups with between 10 and 50,000 siloxane units, preferably between 30 and 10,000 siloxane units, can be mentioned as an example. The length of the dimethiconols can be in the same range.

Dimethicones are commercially available. A particularly well-suited dimethicone is the dimethicone marketed by Dow Corning under the designation DC556. Dimethiconols are also commercially available.

The silicones involve less firm adhesion to the skin or have a lower level of affinity for the skin, than the silicone-free phase, and therefore migrate 'outwardly' after having been applied. They have very good adhesion to the lipophilic layer formed by the component a) and are therefore deposited as a separate layer over same.

In order further to promote that separation into two layers, the component b) contains a fluorosilicone which acts as a 'separating agent'. In addition the fluorosilicone serves to make the material slidable and easy to apply, while however at the same time preventing the material from becoming excessively slippery.

A preferred embodiment involves using, as a particularly well-suited fluorosilicone, perfluorononyl dimethicone, which is particularly well suited as a separating agent. The products marketed under the name Pecosil for example are suitable here. Particularly preferably a perfluorononyl dimethicone of the following formula is used:

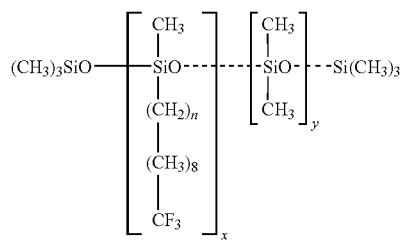

wherein x can be an integer of between 1 and 50 and y can be an integer of between 3 and 500 and n can denote between 0 and 3.

Dimethicone and dimethiconol are preferably contained in the component b) in a ratio of between about 90:10 and 10:90, preferably between 60:40 and 40:60. The fluorosilicone is appropriately used in a proportion of between 0.5 and 10, preferably between 0.8 and 5% by weight, with respect to the overall composition.

In order to impart structure to the layer formed by component b), structure-forming materials which are compatible with the silicones of that phase can additionally be added. Suitable inter alia is a methylphenyl silicone, preferably in a proportion of between 0.2 and 5, particularly preferably between 0.5 and 3% by weight, with respect to the overall composition.

In order to adjust the viscosity of component b) in a suitable range, fillers and thickening agents can also be added to that component, wherein those which are compatible with the silicones are preferred. Talcum, kaolin, starch and modified starch, polytetrafluorothylene powder, nylon powder, boron nitride as well as insoluble metal soaps are listed here as being suitable.

With the above-described constituents the silicone phase affords protection and provides for a 'glossy' appearance. In a preferred embodiment component b), in addition to the constituents forming the protective layer, may also contain compounds which are referred to in the present invention as effect agents. The term effect agents is used here to denote pearl gloss-like, mother-of-pearl-like, iridescent, glittering and luminescent pigments. Mica, pearl gloss agents such as for example titanium dioxide-coated mica, colored mica coated with titanium dioxide and metal oxide, bismuth oxide chloride, coated bismuth oxide chloride, flake-form metal powder of aluminum, brass, bronze, copper, silver and gold can be named here as examples, although that list is in no way definitive.

Component a) contains such pigments which are referred to as flat pigments. In the production procedure those flat pigments are incorporated into the constituents of the component a) and can there be saturated with the solubilisation medium used, generally isoparaffin, and as a result remain in that phase even when they are mixed with the constituents of component b). That provides that those flat pigments migrate into the lower layer upon being applied to the skin. In comparison the effect pigments such as iridescent, glittering and pearl gloss-like pigments are mixed with the constituents of component b) and then remain even upon mixing with the constituents of component a) in the silicone-bearing phase and therefore upon being applied move into the upper layer. That ensures that the gloss and the glittering effect of the pearl gloss-like, iridescent, glittering and glimmering pigments, referred to hereinafter as effect pigments, are not adversely affected by matting pigments which are possibly contained in component a). In addition it is possible in that way to embody for example 'frost' effects insofar as coloring pigments such as red, orange and violet pigments are incorporated into the component a) while metal flakes, iridescing pigments and so forth are incorporated into the silicone phase of the component b) and then lie like a white frost over the colored layer and nonetheless allow it to shine through.

The preparation produced in accordance with the invention has two components which are compatible with each other insofar as they are stable 'in vitro' and can be stored even at fluctuating temperatures over a prolonged period of time without separation phenomena (also referred to as syneresis). The compatibility however is such that, upon being applied to the lips, the preparation spontaneously separates into two layers, wherein a colored and glossy layer remains directly on the lips and seals the surface as a kind of barrier layer so that a transfer-resistant coating is obtained. The components which are selected for the preparation according to the invention are such that, with the shearing forces which occur in the production procedure, no separation occurs, while separation occurs spontaneously when applied to the skin over an area thereof. Separation must therefore be controllable in dependence on the volume of the surface so that stability is afforded with a large volume and a small surface area during storage and spontaneous separation occurs with a small volume and a large surface area as occurs upon application to the skin, in particular the lips.

In order to achieve products with a so-called 'frost effect', it is important for the various kinds of pigments—flat pigments and effect pigments—to be separately incorporated into the components a) and b) respectively. Incorporation of the effect pigments into the silicone phase also has the advantage that the more shearing-sensitive pigments are not exposed to the homogenisation effect and as a result are not destroyed.

A further subject of the invention is therefore a process for the production of a preparation as has been described hereinbefore, wherein polybutene and/or polyisobutene, isoparaffin, wax and/or wax ester are provided and are melted with agitation, flat pigments are added and the mixture is homogenised, in a separate procedure fluorosilicone, dimethicone and dimethiconol and optionally effect pigments are mixed and added to the non-silicone-bearing phase and then the mass is cooled down and introduced into containers.

Homogenisation of the silicone-free phase is effected in per se known manner, for example by means of a three-roll mill or with a corundum disk mill or a colloid mill.

The preparation according to the invention is preferably applied to the lips. A further subject of the invention is therefore a kit comprising a container which contains the preparation and an applicator. The container can be of a per se known configuration, for example in the form of a pot, bowl, tubular container or in some other fashion as is known for lip creams and lipsticks. The applicator can be a brush of different appropriate sizes, a sponge applicator or a spatula. In a particularly preferred embodiment the preparation is contained in a device which is known as Viscomagic wherein the mass is conveyed out of the interior in the required amount on to a flock applicator element and is then distributed on the skin of the lips.

To explain the invention set out hereinafter are two Examples disclosing compositions for lipsticks. In this respect all amounts are specified in % by weight, with respect to the weight of the overall preparation.

|  |  | Example 1 | Example 2 |
|---|---|---|---|
| Phase I | Polybutene | 38.000 | 32.000 |
|  | $C_{11}$-$C_{12}$ isoparaffin | " | 22.000 |
|  | $C_{20}$-$C_{22}$ isoparaffin | 23.500 | " |
|  | Behenyl behenate | 4.000 | " |
|  | Carnauba wax | " | 3.850 |
|  | Isostearyl isostearate | " | 8.700 |
|  | Phenoxyethanol | 0.450 | 0.450 |
| Phase II | Perfluorononyl dimethicone | 2.000 | 1.500 |
|  | Dimethicone | 12.000 | 11.500 |
|  | Dimethiconol | 10.000 | 10.000 |
|  | Phenyl trimethicone | 1.000 | 1.500 |
| Phase III | Non-glossy coloring agents | 3.550 | 3.500 |

-continued

|  |  | Example 1 | Example 2 |
|---|---|---|---|
| Phase IV | Pearl gloss agents, flake-form metal powder | 5.500 | 5.000 |

The constituents of phase I—with the exception of the phenoxyethanol—are put in an evacuatable agitator vessel and melted with agitation until a clear mixture is produced. The non-glossy coloring agents of phase III are added to that mixture and the mixture is then homogenised (three-roll mill, corundum mill or colloid mill). In a separate vessel, the constituents of phase II are homogeneously agitated and then the pearl gloss agents and optionally the flake-form metal powders are smoothly stirred in. The phenoxyethanol is added to the mixture of phase I and phase III and then all partial phases are combined and homogeneously mixed. The batch is now briefly subjected to an operation for the removal of air, cooled to 28-30° C. and introduced into storage containers.

The result obtained is a stable preparation which remains homogeneous for a prolonged period of time. Upon being applied to the lips a transfer-resistant film is formed, which has a very pleasant feel.

The invention claimed is:

1. A water-free preparation for application to the lips comprises a stable homogeneous composition capable of storage without separation into two separate phases which, as soon as it is applied to the lips, separates into two different phases, comprising:
   phase (a) a silicone-free phase comprising at least one of polybutene and polyisobutene, at least one isoparaffin, and at least one of wax and wax ester; and
   phase (b) a silicone-bearing phase comprising at least one fluorosilicone, at least one dimethicone, and at least one dimethiconol, wherein the silicone-free phase (a) forms a lower layer which adheres strongly to the lips and the silicon-bearing phase (b) forms an upper layer which is disposed as a protective layer over the lower layer.

2. A preparation as set forth in claim 1, wherein phase (a) contains at least two polymers selected from polybutene and polyisobutene each of different respective molecular masses.

3. A preparation as set forth in claim 2, wherein phase (a) contains one of a polybutene and polyisobutene having a weight-average molecular mass of less than one million and a second polybutene or polyisobutene of a molecular mass of less than 30,000.

4. A preparation as set forth in claim 2, wherein phase (a) contains one of a polybutene and polyisobutene having a weight-average molecular mass in the range of between 10,000 and 500,000 and a second polybutene or polyisobutene of a molecular mass of between 1,000 and 25,000.

5. A preparation as set forth in claim 2, wherein phase (a) contains one of a polybutene and polyisobutene having a weight-average molecular mass in the range of between 15,000 and 100,000 and a second polybutene or polyisobutene of a molecular mass of between 2,000 and 10,000.

6. A preparation as set forth in claim 1, wherein phase (a) comprises an isoparaffin with a chain length of between 8 and 30 C-atoms.

7. A preparation as set forth in claim 1, wherein phase (a) comprises an isoparaffin with a chain length of between 10 and 24 C-atoms.

8. A preparation as set forth in claim 1, wherein phase (a) contains a combination of isoparaffins of differing volatility.

9. A preparation as set forth in claim 1, wherein the isoparaffin is of low volatility at ambient temperature and evaporates at body temperature within 24 hours.

10. A preparation as set forth in claim 1, wherein the wax is selected from the group consisting of vegetable, animal, mineral, synthetic and mixtures thereof.

11. A preparation as set forth in claim 1, wherein the ester is selected from the group consisting of an ester of a saturated or singly or multiply unsaturated straight-chain or branched fatty acid of a chain length of between C-12 and C-40, and a saturated or singly or multiply unsaturated straight-chain or branched fatty alcohol of a chain length of between C-12 and C-40.

12. A preparation as set forth in claim 1, wherein phase (a) comprises as the ester a fatty acid-fatty alcohol ester.

13. A preparation as set forth in claim 1, further comprising a coloring agent in phase (a).

14. A preparation as set forth in claim 13, wherein the coloring agent is a flat pigment.

15. A preparation as set forth in claim 1, wherein the phase (a) comprises at least one coloring agent selected from the group consisting of inorganic and organic pigments, lakes of organic coloring agents, fluoroesceins, quinoline dyestuffs, triphenyl methane dyestuffs, anthraquinone dyestuffs, and mixtures thereof.

16. A preparation as set forth in claim 1, wherein phase (a) comprises at least one coloring agent selected from the group consisting of titanium dioxide, zinc oxide, iron oxides, chromium oxide, chromium hydroxide, ultramarine, C.I. pigments Red 57:1, Red 49:1, Red 48;1, Red 52:1, Red 41, Red 3, Red 23, Red 112, Red 169, Orange 16, Orange 5, Violet 1, Violet 23, Green 7, Blue 61, Blue 62, Blue 15:1, White 6, Yellow 3, Yellow 13, Yellow 55, Yellow 126, FD and C Red 3, D and C Red 3, 6, 7, 21, 27, 30, 33, 36, 40, FD and C Yellow 5, 6, D and C Yellow 6, 10, and fluorescing coloring agents comprising C.I. 45380, 45370:1, 47000, 47005, 42090, 60730 or 61570.

17. A preparation as set forth in claim 13, wherein the coloring agent is present in a proportion of between 1 and 50% by weight, with respect to the overall composition.

18. A preparation as set forth in claim 13, wherein the coloring agent is present in a proportion of between 5 and 40% by weight, with respect to the overall composition.

19. A preparation as set forth in claim 1, wherein phase (a) and phase (b) are present in a weight ratio of between 10:1 and 1:1.

20. A preparation as set forth in claim 1, wherein phase (a) and phase (b) are present in a weight ratio of between 7:3 and 1:1.

21. A preparation as set forth in claim 1, wherein the phase (a) contains at least one of antioxidants and preserving agents.

22. A preparation as set forth claim 1, wherein phase (b) includes a perfluorononyl dimethicone.

23. A preparation as set forth in claim 1, wherein phase (b) further comprises at least one of pearl gloss agents, metal powders, glittering constituents and iridescing constituents.

24. A preparation as set forth in claim 23, wherein phase (b) further comprises at least one of mica, titanium dioxide-coated mica, colored mica coated with titanium dioxide and metal oxides, bismuth oxide chloride, coated bismuth oxide chloride, flake-form metal powder of aluminum, brass, bronze, copper, silver and gold as a metal pigment.

25. A preparation as set forth in claim 1, wherein the fluorosilicone is present in a proportion of between 1 and 10% by weight, with respect to the overall composition.

26. A preparation as set forth in claim 1, wherein the preparation contains straight-chain non-fluorine-bearing dimethylsiloxanes and hydroxyl group-bearing silicones in a proportion of between 10 and 60% by weight with respect to the overall composition.

27. A preparation as set forth in claim 1, wherein the preparation contains straight-chain non-fluorine-bearing dimethylsiloxanes and hydroxyl group-bearing silicones in a proportion of between 15 and 50% by weight, with respect to the overall composition.

28. A preparation as set forth in claim 24, wherein the pearl gloss and metal pigments are contained therein in a proportion of between 1 and 20% by weight.

29. A preparation as set forth in claim 24, wherein the pearl gloss and metal pigments are contained therein in a proportion of between 3 and 10% by weight.

30. A preparation as set forth in claim 1, having a viscosity of between 500 mPa s and 1500 Pa s, measured with a Bohlin rheometer with a cone-plate system, 4°/40 mm.

31. A preparation as set forth in claim 1, having a rest viscosity at a shearing rate of 0.001/s in a range of between 10 and 1500 Pa s.

32. A preparation as set forth in claim 1, having a rest viscosity at a shearing rate of 0.001/s in a range of between 50 and 1200 Pa s.

* * * * *